United States Patent [19]
Melnik

[11] Patent Number: 4,756,905
[45] Date of Patent: Jul. 12, 1988

[54] INSECT-REPELLENT CAMOUFLAGE COMPOSITION

[76] Inventor: John Melnik, 2670 - 4½ Mile Rd., Racine, Wis. 53402

[21] Appl. No.: 22,755

[22] Filed: Mar. 6, 1987

[51] Int. Cl.$^4$ .............................................. A61K 7/21
[52] U.S. Cl. ...................................... 424/63; 424/405
[58] Field of Search ................ 424/DIG. 10, 63, 405, 424/409, 407

[56] References Cited

U.S. PATENT DOCUMENTS 2,435,005  1/1948  Huppke et al. ......... 424/DIG. 10 X

Primary Examiner—Nancy A. B. Swisher
Attorney, Agent, or Firm—Peter N. Jansson, Ltd.

[57] ABSTRACT

An insect repellent camouflage composition for application to the skin including N,N-diethyl-m-toluamide and camouflage pigment to provide both camouflage and insect repellence by a single application without interference with either function. Some embodiments include a skin-compatible vehicle miscible with the pigment and toluamide, preferably including water, skin oil(s), and emulsifier(s).

19 Claims, No Drawings

INSECT-REPELLENT CAMOUFLAGE COMPOSITION

FIELD OF THE INVENTION

This invention is related generally to insect repellent compositions for application to the skin and, more particularly, to N,N-diethyl-m-toluamide compositions used for certain outdoor activities in which camouflaging the skin is desirable, such as hunting and various military operations.

BACKGROUND OF THE INVENTION

Insect repellents for application to the human skin are widely used by outdoorsmen. Such compositions, which come in the form of liquids, creams, pastes and gels, are rubbed or sprayed on the skin. Covered areas are protected from insect bites by the repellent nature of the composition, which dissuades certain insects, including mosquitoes, from alighting.

The most widely used insect repellent active in use today is N,N-diethyl-m-toluamide, sometimes referred to as "DEET," which is described in U.S. Pat. No. 2,932,665. DEET is very effective in protecting an outdoorsman from insects, provided it is properly applied such that it adequately covers the skin of the user. But insects, such as mosquitoes, frequently will alight on areas where the repellent composition has been "wiped" or "rubbed" off or on areas of weak or uneven coverage.

Maintaining thorough protection of all exposed skin, and thus maintaining effective insect repellence of all exposed skin, is of great importance to many outdoorsmen, particularly hunters such as duck hunters, who remain as motionless as possible in a duck blind for long periods, and military personnel operating in insect infested areas.

Such outdoorsmen often apply camouflage creams and the like to their skin in an effort to obscure their presence to ducks, other game which they are hunting, or the enemy. Such camouflage compositions are heavily and darkly pigmented compositions suitable for application to the skin.

In order for such an outdoorsman to camouflage his skin and protect it from insects, he must apply two separate skin compositions—a camouflage composition and an insect repellent composition. Applying two separate compositions in two separate application steps is both inconvenient and time-consuming for outdoorsmen.

In addition, such piggybacked application of compositions on the skin unfortunately can tend to cause ineffective functioning of one or both of the compositions. For example, if an insect repellent composition is applied just prior to application of a camouflage cream, the insect repellent can be removed or made uneven such that its effectiveness is reduced, at least in certain areas. Or, if an insect repellent is applied after application of a camouflage composition, the camouflage can be removed or, more typically, made uneven and blotchy.

In short, the application of such compositions to the skin seriatim, in either order, leads to ineffectiveness of one or both of the functions they are intended to serve. Most notably, the effectiveness of the composition which is applied first is interrupted or reduced upon application of the composition which is applied second.

OBJECTS OF THE INVENTION

It is an object of this invention to provide improved insect repellent compositions for application to the skin overcoming some of the problems and shortcomings of the prior art, including those mentioned above.

Another object of this invention is to provide an insect repellent composition with improved effectiveness for outdoorsmen who require skin camouflage.

Another object of this invention is to provide an insect repellent composition allowing evenness in camouflage application without sacrificing evenness in insect repellence.

Another object of this invention is to provide effective insect repellence and camouflage for outdoorsmen with a single convenient application to the skin.

These and other important objects will be apparent from the descriptions of this invention which follow.

SUMMARY OF THE INVENTION

This invention is an improved insect repellent composition for application to the skin which provides both effective insect repellence and effective camouflage for hunters, military personnel, and other outdoorsmen. Both functions are effectively served with a single application step, without the aforementioned unevenness and other interference of one function with the other.

The insect repellent composition of this invention has about 10-95% N,N-diethyl-m-toluamide (DEET), present in an insect repellent-effective concentration, and about 5-70% pigment, such amounts being by weight of the total composition. In addition, some embodiments include up to about 85% of a skin-compatible vehicle which is miscible with the DEET and pigment.

In preferred embodiments, the weight ratio of pigment to DEET is from about 1:1 to about 1:5. The most preferable weight ratio is on the order of 1:3. While up to about 85% of a skin-compatible vehicle may be used with the DEET and pigment, amounts of skin-compatible vehicle well below 85% are preferred.

In certain preferred embodiments, the composition is entirely or substantially entirely comprised of DEET and pigment. It has been found that DEET alone suspends the pigment powder(s) in a satisfactory manner and that the resulting mixture provides even repellence and an even application of camouflage without the necessity of any other ingredient in the composition.

Many different pigment materials of various kinds may be used. In preferred embodiments, the pigment includes metal oxides, such as iron oxide (black), titanium dioxide (white), and chromium oxide, which is sometimes referred to as ultramarine green, or mixtures thereof. Other pigment materials, such as ultramarine blue, may also be used alone or in combination with the preferred metal oxides. Iron oxide alone has been found to be effective as well.

The skin-compatible vehicle included in certain preferred embodiments is miscible with the pigment and DEET. A wide variety of such skin-compatible vehicles may be used, including without limitation solutions and emulsions. Such vehicles may be made of a variety of substances. Skin-compatible emulsions will include water, one or more skin oils, and one or more emulsifiers. Emulsion stabilizing agents are also preferably used.

Many different skin oils are suitable for use in such skin-compatible vehicles, including mineral oil, lanolin oil, white patrolatum, certain silicon oils, almond oil, olive oil, and various oil blends.

Such skin-compatible vehicles mauy also include: skin moistening agents, such as propylene glycol; emollients, such as cetyl alcohol, talc and kaolin; skin protectants, such as stearic acid; and various preservatives, fillers, and other ingredients, usually in minor amounts.

Appropriate emulsifiers will be chosen depending on the nature of the intended formulation and the oil-soluble and water-soluble ingredients requiring emulsification. Suitable emulsifiers in certain preferred formulations include triethanalamine and sorbitan sesquioleate. Emulsion stabilizers, such as glyceryl stearate, cetyl alcohol, and talc may also be used.

The dual-purpose insect repellent compositions of this invention are preferably liquids, either mixtures or emulsions. They may be in the form of a cream, a paste, or even a gel-like stick which may be applied to the skin.

There are no special requirements for methods of preparing the compositions of this invention. The DEET, the pigment(s), and the ingredients of their skin-compatible vehicle may be mixed in any reasonable order, with attention being given to which parts are oil-soluble and which are water-soluble, if an emulsion is to be formed.

When the composition is limited to DEET and pigments, the pigments preferably are first dry-blended, if more than one pigment powder is used. Then the pigments are mixed with the DEET, with thorough stirring to disperse the powder in the DEET.

When an additional skin-compatible vehicle is used, it may be mixed with the DEET-pigment mixture. Or the ingredients may be mixed in a different manner and different order.

When an emulsion composition is being prepared, the pigment powders and any talc, kaolin and fillers are preferably first dry-blended in a first vessel. The water, DEET, and any water-soluble ingredients are mixed thoroughly in a second vessel. In a third vessel, the oils and oil-soluble constituents are heated and mixed. Then the contents of the second vessel are heated and the contents of the first and third vessels are added to it with agitation. The emulsifier is then added and the contents are stirred continually until a uniform emulsion is formed and cooled to room temperature.

The composition of this invention may be packaged in a variety of ways, the best way depending on the viscosity of the composition and other factors. Acceptable packaging includes glass bottles, squeeze bottles, tubes, and jars.

A wide variety of other mixing techniques and packaging can be used.

As noted, acceptable amounts of DEET range between about 10% and about 95% by weight of the entire composition. Less than about 10% DEET usually provides less than an effective insect repellence, while greater than 95% leaves insufficient capacity in the composition for an effective amount of pigment.

While the amount of pigment is between about 5% and about 70% by weight of the composition, the middle portion of such range is preferred. Less than about 5% pigment gives an unacceptable camouflage effect, depending on the pigment which is used, while over about 70% pigment provides physical qualities in the final composition which are unacceptable. More specifically, above that level the composition is too thick and too difficult to apply to the skin to be useful.

While the additional skin-compatible vehicle may be used at a level of up to 85%, at the upper level only minimally acceptable amounts of DEET and pigment may be used. It is preferred that much lower, though substantial, amounts of a skin-compatible vehicles be used.

The skin-compatible vehicle is a vehicle for both the DEET and the pigment. Such vehicle serves, along with the DEET, as a carrier for the pigment.

As noted, the preferred ratio of pigment to DEET is from about 1:1 to about 1:5. Within that range, the insect repelling and camouflaging functions are both well served. With pigment at a higher level, the composition becomes thick and rather difficult to use, depending on the nature and amount of skin-compatible vehicle, if any. With pigment at a lower level, the camouflage tends to become less effective.

EXAMPLE 1

An insect repellent composition was made using the following formulation:

| Ingredient | % by weight of total |
| --- | --- |
| DEET | 75.0 |
| Iron oxide powder | 25.0 |

The DEET and iron oxide are mixed well in a mixing vessel and form a freely flowing liquid composition which is then packaged in a squeeze bottle. The composition, which should be agitated a bit prior to each usage, provides both excellent insect repellence and an even camouflage for human skin.

EXAMPLE 2

An insect repellent composition was made using the following formulation:

| Ingredient | % by weight of total |
| --- | --- |
| DEET | 75.0 |
| Iron oxide powder | 10.0 |
| Titanium dioxide powder | 5.0 |
| Chromium oxide powder | 5.0 |
| Ultramarine blue powder | 5.0 |

The DEET and powders are mixed well in a mixing vessel and form a freely flowing liquid composition which is then packaged in a squeeze bottle. This composition provides both excellent insect repellence and an even camouflage for human skin.

EXAMPLE 3

A composition was made using the following formulation:

| Ingredient | % by weight of total |
| --- | --- |
| DEET | 83.0 |
| Iron oxide powder | 10.0 |
| Titanium dioxide powder | 2.0 |
| Chromium oxide powder | 3.0 |
| Ultramarine blue powder | 2.0 |

The DEET and pigment powders are mixed well in a mixing vessel and form a freely flowing liquid composition which is then packaged in a squeeze bottle. This composition provides excellent insect repellence and good camouflage for human skin.

EXAMPLE 4

A composition was made using the following formulation:

| Ingredient | % by weight of total |
| --- | --- |
| DEET | 50.0 |
| Iron oxide powder | 50.0 |

The DEET and powders are mixed well in a mixing vessel and form a somewhat thick mixture which may be packaged in a jar. The composition has good repellence and camouflage qualities.

EXAMPLE 5

An insect repellent composition was made using the following formulation:

| Ingredient | % by weight of total |
| --- | --- |
| DEET | 30.0 |
| Iron oxide powder | 70.0 |

The DEET and powders are mixed well in a mixing vessel and form a thick mixture which may be packaged in a jar. This composition is rather hard to spread on the skin, and leaves a heavy coating of pigment solids on the skin. Insect repellency is acceptable.

EXAMPLE 6

An insect repellent composition was made using the following formulation:

| Ingredient | % by weight of total |
| --- | --- |
| DEET | 94.0 |
| Iron oxide powder | 6.0 |

The DEET and powders are stirred well in a mixing vessel and form a runny mixture which may be packaged in a bottle. This composition is preferably shaken before use. A heavy coating is required in order to provide a satisfactory camouflage. Insect repellency is excellent.

EXAMPLE 7

An insect repellent composition was made using the following formulation:

| Ingredient | % by weight of total |
| --- | --- |
| DEET | 37.5 |
| Iron oxide powder | 8.0 |
| Titanium dioxide powder | 1.5 |
| Chromium oxide powder | 1.5 |
| Ultramarine blue powder | 1.5 |
| Water | 32.5 |
| Mineral oil | 5.0 |
| Talc | 2.5 |
| Propylene glycol | 2.0 |
| Glyceryl stearate | 1.5 |
| Magnesium aluminum silicate | 1.5 |
| Stearic acid | 1.5 |
| Cetyl alcohol | 1.5 |
| Triethanolamine | 0.7 |
| Kaolin | 1.0 |
| Methylparaben | 0.2 |
| Propylparaben | 0.1 |

The talc, kaolin, magnesium aluminum silicate, and the pigment powders are dry-blended in a first vessel. In a second vessel, the DEET, water, propylene glycol, and methylparaben are thoroughly mixed. The mineral oil, glyceryl stearate, stearic acid, cetyl alcohol and propylparaben are combined in a third vessel and heated to 75 degrees C. and mixed. The second vessel contents are then heated to 75 degrees C. and the first and third vessel contents are added to the second vessel with agitation. The triethanolamine is then added and stirring continues until a uniform emulsion is formed and is cooled to room temperature. The composition is packaged in a squeeze bottle.

An easily applied liquid is formed which provides very good repellency and camouflage.

EXAMPLE 8

A composition was made using the following formulation:

| Ingredient | % by weight of total |
| --- | --- |
| DEET | 75.0 |
| Iron oxide powder | 2.0 |
| Titanium dioxide powder | 1.0 |
| Chromium oxide powder | 1.0 |
| Ultramarine blue powder | 1.0 |
| Water | 4.0 |
| Mineral oil | 8.0 |
| White petrolatum | 7.0 |
| Sorbitan sesquioleate | 0.6 |
| Lanolin alcohol extract | 0.4 |

The pigment powders are dry-blended. Then the water and DEET are added and mixed thoroughly, while heating to 75 degrees C. In a second vessel, the mineral oil, white petrolatum, lanolin alcohol extract, and sorbitan sesquioleate are mixed and heated to 70 degrees C., and then added to the DEET-water-pigment mixture. After stirring until the composition has cooled to room temperature, the composition is packaged in a squeeze bottle.

An easily applied liquid is formed which provides very good repellency but marginal camouflage.

EXAMPLE 9

An insect repellent composition was made using the following formulation:

| Ingredient | % by weight of total |
| --- | --- |
| DEET | 50.0 |
| Iron oxide powder | 6.5 |
| Titanium dioxide powder | 2.0 |
| Chromium oxide powder | 2.0 |
| Ultramarine blue powder | 2.0 |
| Water | 24.4 |
| Mineral oil | 3.7 |
| Talc | 1.9 |
| Propylene glycol | 1.5 |
| Glyceryl stearate | 1.1 |
| Magnesium aluminum silicate | 1.1 |
| Stearic acid | 1.1 |
| Cetyl alcohol | 1.1 |
| Triethanolamine | 0.5 |
| Kaolin | 0.8 |
| Methylparaben | 0.2 |
| Propylparaben | 0.1 |

Blend using the method set forth in Example 7. Then package in a sqeeze bottle. An easily applied liquid is formed which provides good repellency and camouflage.

EXAMPLE 10

A composition was made using the following formulation:

| Ingredient | % by weight of total |
| --- | --- |
| DEET | 50.0 |
| Iron oxide powder | 6.5 |
| Titanium dioxide powder | 2.0 |
| Chromium oxide powder | 2.0 |
| Ultramarine blue powder | 2.0 |
| Water | 7.5 |
| Mineral oil | 15.0 |
| White petrolatum | 13.1 |
| Sorbitan sesquioleate | 1.1 |
| Lanolin alcohol extract | 0.8 |

Blend using the method of Example 8. Then package in a squeeze bottle.

An easily applied liquid is formed which provides good repellency and good camouflage.

EXAMPLE 11

An insect repellent composition was made using the following formulation:

| Ingredient | % by weight of total |
| --- | --- |
| DEET | 10.0 |
| Iron oxide powder | 12.0 |
| Titanium dioxide powder | 2.0 |
| Chromium oxide powder | 4.0 |
| Ultramarine blue powder | 2.0 |
| Water | 45.5 |
| Mineral oil | 7.0 |
| Talc | 3.5 |
| Propylene glycol | 2.8 |
| Glyceryl stearate | 2.1 |
| Magnesium aluminum silicate | 2.1 |
| Stearic acid | 2.1 |
| Cetyl alcohol | 2.1 |
| Triethanolamine | 1.0 |
| Kaolin | 1.5 |
| Methylparaben | 0.2 |
| Propylparaben | 0.1 |

Blend using the method set forth in Example 7. Then package in a squeeze bottle.

An easily applied liquid is formed which provides good camouflage and even, but marginal, insect repellence.

EXAMPLE 12

An insect repellent composition was made using the following formulation:

| Ingredient | % by weight of total |
| --- | --- |
| DEET | 10.0 |
| Iron oxide powder | 5.0 |
| Water | 17.0 |
| Mineral oil | 34.0 |
| White petrolatum | 29.7 |
| Sorbitan sesquioleate | 2.6 |
| Lanolin alcohol extract | 1.7 |

Blend using the method of Example 8, although no initial dry blending step is needed. Then package in a squeeze bottle.

An easily applied liquid is formed which provides evenly spread, but marginal, repellency and only very light camouflage, even when heavily applied.

While the principles of this invention have been described in connection with specific embodiments, it should be understood clearly that these descriptions are made only by way of example and are not intended to limit the scope of the invention.

What is claimed:

1. An insect repellent composition for application to the skin, comprising:
   about 10-95% N,N-diethyl-m-toluamide by weight of the composition present in an insect repellent-effective concentration; and
   about 5-70% skin coloring pigment by weight of the composition,
   whereby camouflage and insect repellence are both provided by a single application without interference with either.

2. The insect repellent composition of claim 1 wherein the pigment comprises metal oxide pigment(s).

3. The insect repellent composition of claim 2 wherein the pigment comprises iron oxide.

4. The insect repellent composition of claim 1 wherein the weight ratio of pigment to N,N-diethyl-m-toluamide is from about 1:1 to about 1:5.

5. The insect repellent composition of claim 4 wherein the weight ratio of pigment to N,N-diethyl-m-toluamide is about 1:3.

6. The insect repellent composition of claim 1 consisting of N,N-diethyl-m-toluamide and pigment.

7. The insect repellent composition of claim 6 wherein the weight ratio of pigment to N,N-diethyl-m-toluamide is from about 1:1 to about 1:5.

8. The insect repellent composition of claim 7 wherein the weight ratio of pigment to N,N-diethyl-m-toluamide is about 1:3.

9. The insect repellent composition of claim 6 wherein the pigment comprises metal oxide pigment(s).

10. The insect repellent composition of claim 9 wherein the pigment comprises iron oxide.

11. The insect repellent composition of claim 1 further comprising skin-compatible vehicle miscible with said pigment and toluamide.

12. The repellent composition of claim 11 wherein the vehicle includes an emulsion comprising water, skin oil(s), emulsifier(s), and emulsion stabilizing agent(s).

13. The insect repellent composition of claim 11 wherein the pigment comprises metal oxide pigment(s).

14. The insect repellent composition of claim 13 wherein the pigment comprises iron oxide.

15. The insect repellent composition of claim 11 wherein the weight ratio of pigment to N,N-diethyl-m-toluamide is from about 1:1 to about 1:5.

16. The insect repellent composition of claim 15 wherein the weight ratio of pigment to N,N-diethyl-m-toluamide is about 1:3.

17. The insect repellent composition of claim 15 wherein the pigment comprises metal oxide pigment(s).

18. The insect repellent composition of claim 17 wherein the pigment comprises iron oxide.

19. An insect repellent composition for application to the skin, comprising:
   about 10-95% N,N-diethyl-m-toluamide by weight of the composition present in insect repellent-effective concentration;
   about 5-70% skin coloring pigment; and
   up to about 85% of a skin-compatible vehicle miscible with said pigment and toluamide, said vehicle including water, skin oil(s), and emulsifier(s),
   whereby camouflage and insect repellence are both provided by a single application without interference with either.

* * * * *